United States Patent [19]

Kolobow

[11] Patent Number: 5,186,167
[45] Date of Patent: Feb. 16, 1993

[54] CATHETER TIP FOR INTRATRACHEAL VENTILATION AND INTRATRACHEAL PULMONARY VENTILATION

[75] Inventor: Theodor Kolobow, Rockville, Md.

[73] Assignee: The United States of America as represented by the Department of Health and Human Services, Washington, D.C.

[21] Appl. No.: 702,479

[22] Filed: May 20, 1991

Related U.S. Application Data

[63] Continuation-in-part of Ser. No. 606,967, Oct. 31, 1990.

[51] Int. Cl.$^5$ .............. A61M 16/00; A62B 9/06; A62B 7/00; F15C 1/08
[52] U.S. Cl. .............. 128/207.14; 128/204.24
[58] Field of Search .............. 128/200.26, 207.14, 128/207.15, 204.18, 204.24, 204.25; 604/94, 96

[56] References Cited

U.S. PATENT DOCUMENTS

| | | | |
|---|---|---|---|
| 3,599,642 | 8/1971 | Tindel | 128/207.14 |
| 3,983,879 | 10/1976 | Todd | 604/96 |
| 4,020,849 | 5/1977 | Jackson | 128/207.15 |
| 4,082,093 | 4/1978 | Fry et al. | 128/204.25 |
| 4,141,356 | 2/1979 | Smargiassi | 128/204.23 |
| 4,202,330 | 5/1980 | Jariabka | 128/204.18 |
| 4,224,939 | 9/1980 | Lang | 128/205.13 |
| 4,232,667 | 11/1980 | Chalon et al. | 128/203.26 |
| 4,421,113 | 12/1983 | Gedeon et al. | 128/204.23 |
| 4,593,690 | 6/1986 | Sheridan et al. | 128/207.15 |
| 4,652,258 | 3/1987 | Drach | 604/96 |
| 4,716,896 | 1/1988 | Ackerman | 128/200.26 |
| 4,773,411 | 9/1988 | Downs | 128/204.18 |
| 4,805,982 | 7/1989 | Erlich et al. | 604/96 |
| 4,892,095 | 1/1990 | Nakhgevany | 128/207.14 |

FOREIGN PATENT DOCUMENTS

| | | | |
|---|---|---|---|
| 0245142 | 11/1987 | European Pat. Off. | 128/207.14 |
| 8806906 | 9/1988 | World Int. Prop. O. | 128/200.26 |
| 8902761 | 4/1989 | World Int. Prop. O. | 128/207.14 |

Primary Examiner—Edgar S. Burr
Assistant Examiner—Kimberly L. Asher
Attorney, Agent, or Firm—Lowe, Price, LeBlanc & Becker

[57] ABSTRACT

A method and apparatus for intratracheal ventilation (ITV) and intratracheal pulmonary ventilation (ITPV) in which a catheter positioned in a patient's trachea at the carina supplies a constant supply of fresh oxygen containing gas to flush anatomical dead space. By positioning the catheter in the patient's trachea, the dead space of the trachea is bypassed and the trachea is only utilized for expiration. The catheter includes a catheter tip which directs the constant supply of fresh oxygen containing gas in a manner so as to create sub-atmospheric pressures near the carina and thus allows control of intratracheal airway pressures during the entire respiratory cycle and prevents overinflation of the lungs.

8 Claims, 3 Drawing Sheets

CATHETER TIP FOR INTRATRACHEAL VENTILATION AND INTRATRACHEAL PULMONARY VENTILATION

RELATED APPLICATIONS

This application is a continuation-in-part of U.S. patent application Ser. No. 07/606,967, filed Oct. 31, 1990.

TECHNICAL FIELD

The present invention relates to intratracheal ventilation and intratracheal pulmonary ventilation methods and apparatus. More particularly, the present invention relates to catheters which are used for delivering fresh air and oxygen mixtures to the trachea and lungs of a subject.

BACKGROUND ART

Congenital diaphragmatic hernia (CDH) currently carries a mortality in excess of 50 percent. Presently, there exists a need for a reliable procedure for providing the necessary ventilation treatment for patients suffering from CDH.

Recent laboratory and clinical evidence strongly implicates mechanical ventilation (MV) at high peak inspiratory pressure (PIP) in the emergence of respiratory distress syndrome (RDS) in the neonate, child and adult. Recovery from severe lung injury is oftentimes facilitated through the use of extracorporeal membrane oxygenation (ECMO), or extracorporeal carbon dioxide removal ($ECCO_2R$), while airway pressures are markedly reduced (lung rest); here, the bulk of $CO_2$ is removed by the extracorporeal membrane lung (ML), allowing lower tidal volumes (VT), respiratory rates (RR), and PIP. Such lung rest cannot be attained only with the use of an extracorporeal ML.

Conventional mechanical pulmonary ventilation as presently utilized is not considered effective at very high respiratory rates, in part because of unavoidable dead space ventilation.

The effect of the anatomical dead space on $CO_2$ removal has been well recognized. In the adult and child, MV (or spontaneous breathing) at frequencies in excess of 60/min is oftentimes not effective.

Although work has been made in the field of pulmonary ventilation, there remains a need for a method and apparatus which allows for respiratory rates which are well above what is presently considered practical.

U.S. Pat. No. 4,082,093 to Fry et al discloses the use of a compensator valve for use with a ventilation system. A positive end expiratory pressure (PEEP) valve is also furnished to maintain an artificial residual pressure in the lungs. The magnitude of PEEP may be varied from cycle to cycle. The compensator valve functions to hold the lung pressure constant at the end of the expiratory cycle.

U.S. Pat. No. 4,141,356 to Smargiassi discloses a respiratory system with both assisted and spontaneous modes of breathing. A control circuit responds to the patient's breathing pattern to alter the system between the two modes, in accordance with a predetermined pattern. As illustrated in FIG. 1, the system also includes regulators 10 and 12 which are used to feed a mixture of both air and oxygen.

U.S. Pat. No. 4,202,330 to Jariabka discloses a small tube 13 which is inserted into the trachea for administering oxygen. The tube is connected to a conduit 20 which is connected at 31 to a valving means 30. A second conduit 40 is connected to the inlet 32 of the valve and the other end of the conduit is connected to an oxygen supply 50 which supplies oxygen at a low temperature.

U.S. Pat. No. 4,224,939 to Lang discloses a pulmonary ventilation system in which a respirator feeds air at a controllable pressure, volume, rate, and respiratory frequency to a humidifier. The humidifier is supplied with sterile, heated water. Tube sections 9 and 12 which supply the conditioned air to an endotracheal tube are connected to an inflatable bag 10 by tee 11.

U.S. Pat. No. 4,232,667 to Chalon et al discloses a ventilating system in which both oxygen and an anaesthetic are controllably passed by a flow meter through an inspiratory limb 16 and a small endotracheal tube which is positioned at the approximate level of the carina. An expiratory limb 18 surrounds the inspiratory limb 16. The expiratory limb is connected to an expiratory valve 34. The limbs are provided with spacing ribs 20 to prevent kinking.

U.S. Pat. No. 4,421,113 to Gedeon et al discloses a lung ventilator for carrying out mandatory minute volume (MMV) treatment. The breathing gas source delivers a volume of gas which is at least equal to the maximum volume that may be required. An inspiratory line is connected to the patient's airway for spontaneous breathing. A ventilator is connected to the breathing gas source and is actuated by a signal to deliver a mandatory breath of a predetermined tidal volume to the patient.

U.S. Pat. No. 4,773,411 to Downs discloses a respiratory method and apparatus which establishes a continuous positive airway pressure (CPAP) to enhance functional residual capacity (FRC). Instead of imposing cycles of elevated airway pressure above a CPAP, airway pressure release ventilation (APRV) is utilized to achieve augmentation of alveolar ventilation and carbon dioxide excretion through intermittent cycles of reduced airway pressure below the CPAP pressure level. Breathing gas may be supplied by a variety of devices including a tight fitting tracheal tube.

U.S. Pat. No. 4,593,690 to Sheridan et al discloses an endotracheal tube having an inflatable balloon cuff which is designed so a to be bendable in various directions.

U.S. Pat. No. 4,716,896 to Ackerman discloses an endotracheal tube 40 which is inserted through the mouth of a patient. Within the endotracheal tube is a catheter 10 which delivers a fluid. The catheter has apertures 18a and 18b at its distal end. The catheter may be made of various plastic materials.

U.S. Pat. No. 4,892,095 to Nakhgevany discloses an endotracheal tube having a diffuser 22 at its end.

The present invention is an improvement over existing methods and apparatus utilized in pulmonary ventilation.

DISCLOSURE OF THE INVENTION

It is according one object of the present invention to provide an apparatus for intratracheal and intratracheal pulmonary ventilation which allows for low peak airway pressures and respiratory rates well beyond what is presently considered practical.

Another object of the present invention is to provide an apparatus for intratracheal pulmonary ventilation which allows for reduced end expiratory intratracheal airway pressures.

A further object of the present invention is to provide a catheter for delivering free air and oxygen mixtures to the trachea and lungs of a subject.

A still further object of the present invention is to provide a catheter having a novel tip design.

An even further object of the present invention is a method of utilizing a novel catheter to control intratracheal airway pressures during the expiratory cycles of intratracheal ventilation.

According to the present invention there is provided a method of providing ventilatory assistance to a patient which comprises:

positioning a distal end of a catheter in an area near the carina of a patient;

supplying a continuous supply of an oxygen containing gas mixture to the patient through the catheter; and directing said supplied oxygen containing gas mixture from the distal end of the catheter so as to create a sub-atmospheric pressure beyond the distal end of the catheter.

The present invention further provides a catheter for providing ventilatory assistance which comprises a catheter tip positioned at a distal end of the catheter, which catheter tip includes means for directing a flow of gas from the catheter tip in a direction which is opposed to a distal end of the catheter tip.

BRIEF DESCRIPTION OF THE DRAWINGS

The present invention will now be described with reference to the annexed drawings, which are given by way of non-limiting examples only in which.

BEST MODE FOR CARRYING OUT THE INVENTION

Figure 1:
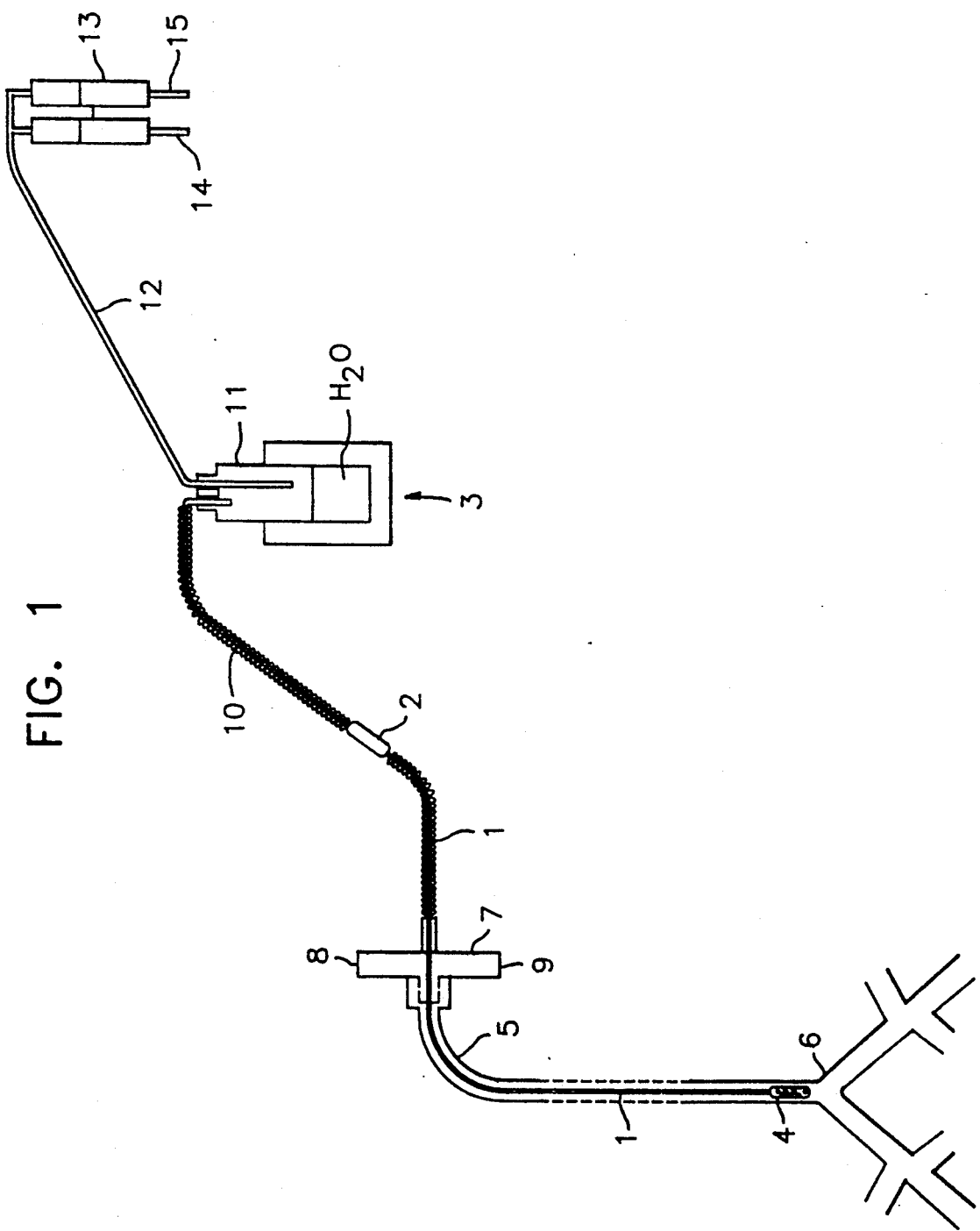
FIG. 1 is a schematic diagram illustrating the ventilation system utilized according to one embodiment of the present invention.

The present invention is directed to a method of intratracheal ventilation (ITV) or intratracheal pulmonary ventilation (ITPV) in which fresh, humidified air/oxygen is introduced at a constant flow rate through a patient's trachea at a position adjacent or near the patient's carina.

In operation, the fresh, humidified air/oxygen is introduced through a very small catheter with a diffuser at its distal end which is placed through an endotracheal or tracheostomy tube, or may be possibly passed percutaneously to rest at the level of the carina. The continuous gas flow is provided at a rate of about 2 to 4 times anatomical dead space/breath. Dead space, as described below, is determined from the volume of the trachea and tracheostomy or endotracheal tube utilized, which, for example in an adult is about 120 cc.

The method of the present invention may be utilized either with or without conventional mechanical ventilation. When utilized without conventional mechanical ventilation, the ITV method of the present invention may be utilized in combination with CPAP. With continuous gas flow, in the constant or continuous positive airway pressure (CPAP) mode the breathing is controlled by the patient. In the ITPV controlled ventilation mode of operation which does not utilize conventional mechanical ventilation, a timed expiratory valve sets the respiratory rate while a minute flow of air/oxygen determines tidal volume (VT)/breath and hence peak inspiratory pressure (PIP). In this mode the trachea is bypassed, since the fresh air/oxygen is introduced at the patient,s carina, and the trachea is therefore used only for expiration. By bypassing the trachea, the anatomical dead space is effectively reduced so that fresh air/oxygen flow rates of approximately 0.5 of the anatomical dead space/breath are acceptable. In the ITPV mode it has been determined that suitable respiratory rates of 10-120/min. or higher may be used.

When used in conjunction with a conventional mechanical ventilation (MV), the MV is operated in the pressure control mode at low tidal volumes (VT), and hence low peak inspiratory pressure (PIP), with RR adjusted to effect adequate alveolar ventilation.

The method of the present invention effectively eliminates the anatomical dead space ventilation, thereby allowing respiratory rat beyond what is now considered practical. As an after effect, the peak airway pressures remain very low, thus avoiding further harm or aggravation to a patient whose lungs are damaged.

The technique of the present invention is distinct from high frequency ventilation, as tidal volumes remain within the normal range, governed by the compliance of individual lung units; unlike high frequency ventilation/oscillation, with much lower tidal volumes, and very much higher respiratory/oscillatory rates. In laboratory studies, excellent gas exchange was accomplished in lungs as small as 12% of normal volume at very low peak airway pressures.

In studies in healthy animals conducted during the course of the present invention, VT has been reduced as low as 1-2 ml/kg, while keeping PIP at 3-4 cm $H_2O$ above PEEP, at frequencies of 120/min. No long term adverse effects resulted utilizing the method/apparatus of the present invention.

The use of ITV alone, or the use of ITV with CPAP, or the use of ITV in combination with a convention MV, greatly facilitates alveolar ventilation both in the low and high frequency range. This mode of ventilation both is distinct from high frequency ventilation, as small or near normal tidal volumes can be used while still effecting excellent $CO_2$ removal.

When the anatomical dead space is continuously flushed with fresh air/oxygen, useful ventilation can be extended to well over 60/min. This allows high RR and low VT, and hence low PIP, greatly reducing, or eliminating high airway pressure induced lung injury.

FIG. 1 is a schematic diagram illustrating the ventilation system utilized according to one embodiment of the present invention. As illustrated in FIG. 1, a small catheter 1 is connected at one end by an adapter 2, e.g., silicone connector, to a means 3 for humidifying and controlling the temperature of an air/oxygen feed.

The distal end of the catheter 1 includes a diffuser 4 which, in use is positioned through a tracheostomy or endotracheal tube 5 to a level adjacent or near a patient,s carina 6. The diffuser 4 is preferably formed integral to the distal end of the catheter and is made from suitable material for medical applications, e.g., silicone rubber. Likewise, the catheter is made from suitable material for medical applications, e.g., silicone or teflon. In a preferred embodiment, the diffuser includes a detectable marker or tag such as a radio opaque tantalum marker which may be utilized to assure proper positioning of the diffuser adjacent or near the patient's carina.

Figure 2:
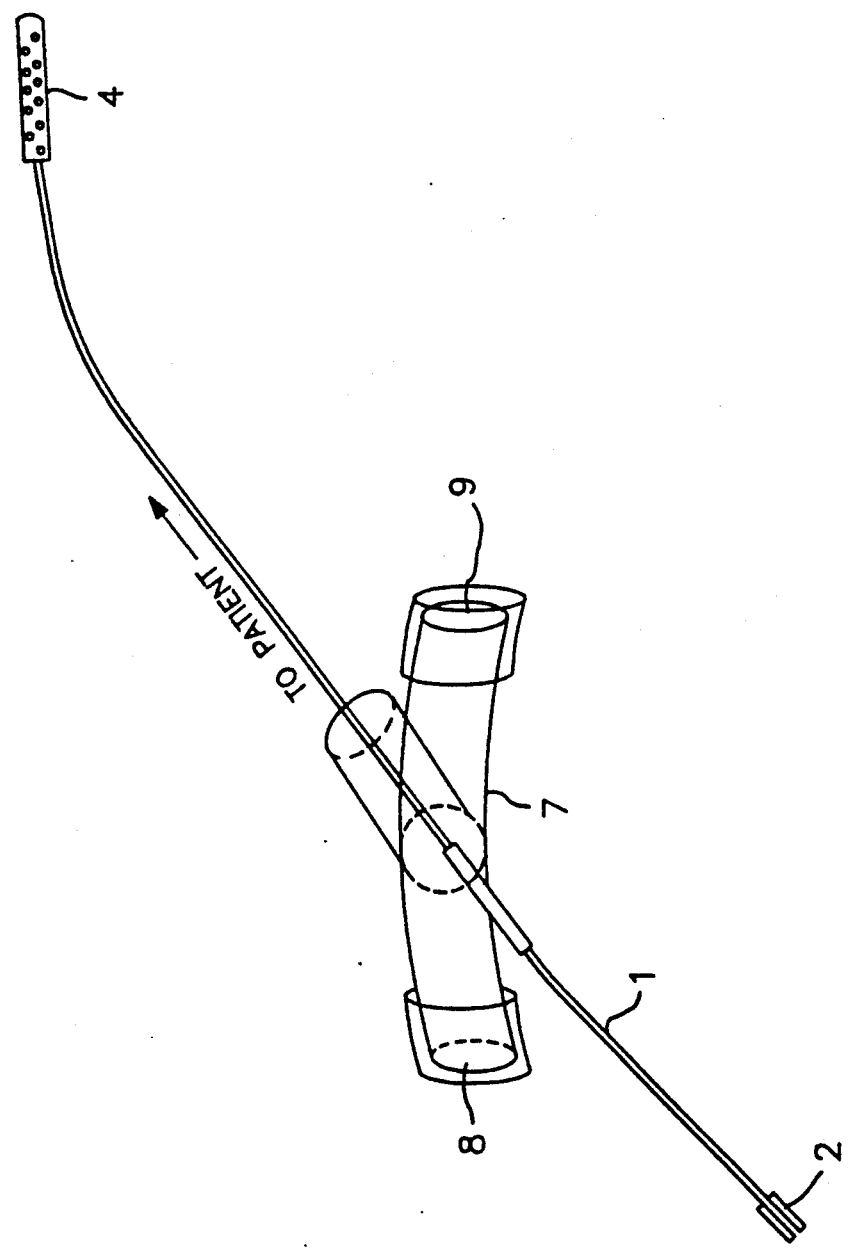
FIG. 2 is a schematic diagram illustrating the catheter utilized in accordance with one embodiment of the present invention.

As illustrated in FIGS. 1 and 2, the catheter is passed through a conventional fitting 7 which is connected to the tracheostomy or endotracheal tube 5 and includes ports 8 and 9 which may be connected to a mechanical ventilator, including a balloon, and a positive end expiratory pressure regulator, respectively. According to the present invention the fitting 7 is modified as illustrated to allow passage of the catheter 1 through the tracheostomy or endotracheal tube 5.

The means 3 for humidifying and controlling the temperature of an air/oxygen feed is connected to adapter 2 by a sufficient length of tubing 10. In order to ensure that the temperature of the air/oxygen feed is maintained after being adjusted by the means for humidifying and controlling the temperature of an air/oxygen feed, both the tubing 10 and the portion of the catheter which extends from fitting 7 to the tubing 10 are covered or wrapped by a suitable insulating material such as multiple layers of a thin plastic wrap.

The means 3 for humidifying and controlling the temperature of an air/oxygen feed includes a reservoir 11 which is filled with sterile water and heated by a suitable means such as an electrical heater to a temperature of about 37° C. The top of the reservoir 11 is closed by a cover having two ports or fittings to which an air/oxygen supply tubing 12 and tubing member 10 are connected. Air/oxygen is supplied to the air/oxygen supply tubing 12 from a suitable, metered source 13 of air and oxygen which allows for individual metering of both a source of air 14 and oxygen 15 at room temperature.

FIG. 2 is a schematic diagram illustrating the catheter utilized in accordance with one embodiment of the present invention. As illustrated in FIG. 2, the diffuser 4 is preferably formed integral to the distal end of the catheter and includes a plurality of gas passage ports along the length thereof.

In operation, the catheter is passed through the tracheostomy or endotracheal tube 5 so as to position the diffuser 4 at or near the level of the patient's carina. In order to prevent kinking of the catheter, the catheter may be inserted and positioned with the aid of a guide wire.

In operation, the oxygen content of the air/oxygen mixture supplied to the catheter may be adjusted from 21.1 to 100 percent. Thus the mixture may range from pure air to pure oxygen as necessary.

In tests utilizing the system illustrated in FIG. 1, a gas flow rate of about 8.4 liters/minute was provided utilizing a gas flow pressure of about 5 psi; a gas flow rate of about 13.4 liters/minute was provided utilizing a gas flow pressure of about 10 psi; and a gas flow rate of about 17.7 liters/minute was provided utilizing a gas flow pressure of about 15 psi.

In tests utilizing the system illustrated in FIG. 1, the dead space of the trachea and tracheostomy or endotracheal tube was determined to be about 120 cc. Thus, utilizing a recommended gas flow of 2 times the dead space/breath when used in conjunction with a mechanical ventilator, or while on CPAP, or on spontaneous unassisted ventilation, the following equation was utilized to determine constant gas flow rates at predetermined respiratory rates:

*Flow Rate = Respiratory Rate × 2 × Dead Space*

From this equation the following flow rates were calculated utilizing the system illustrated in FIG. 1.

| Respiratory Rate | Flow Rate |
| --- | --- |
| 20 min$^{-1}$ | 4800 cc/min |
| 40 min$^{-1}$ | 9600 cc/min |
| 60 min$^{-1}$ | 14400 cc/min |
| 80 min$^{-1}$ | 19200 cc/min |

When used as ITPV, the required flow rates are greatly reduced, as gas flow rises only slightly at higher respiratory rates, the reason being that all fresh gas is delivered bypassing the tracheal dead space.

The following non-limiting examples are presented to illustrate features and characteristics of the present invention which is not to be considered as being limited thereto. In the examples and throughout lung percentages are by volume.

EXAMPLE 1

In a series of young healthy lambs of approximately 10 kg the left lung (total of 43%), plus the right lower and cardiac lobe (81%), plus the right middle lobe (RML)(88%) were progressively excluded from gas exchange. In some tests the lobes were surgically removed; in other tests the bronchi and pulmonary arteries to the respective lobes were tied.

Lambs were sedated and paralyzed. Tests were conducted utilizing a controlled mode MV (Servo 900 C), a tidal volume (VT) not more than 20 ml/kg based on remaining lung mass, a respiratory rate (RR) up to 120/min, a PIP of 12-15 cm H2O and a PEEP of 3 cm H2O.

Those lambs with the right upper lobe (RUL) and RML (19% remaining lungs) were weaned to room air on MV within 48 hours. Ventilating RUL (12% of lung mass) alone required higher VT and PIP to provide adequate alveolar ventilation, but resulted in RDS and death within 8 hours.

EXAMPLE 2

In this example, the ventilation system/method of the present invention was tested for comparison with the results from Example 1 above.

A continuous flow of a humidified mixture of air and oxygen was passed directly into the trachea at the level of the carina through a diffuser at a rate 4 times the projected tidal volume for the remaining lung, effectively eliminating the tracheal anatomical dead space. A single valve controlled the expiration frequency.

In this example, lambs with only RUL remaining were weaned to room air within 2 hours, at a RR of 60-120/min; PIP 14-19 cm H2O, respectively; PEEP 3 cm H2O; mean pulmonary artery pressure (mPAP) 30-35 mm Hg. The same lungs subsequently managed on conventional MV at "optimal" settings, following a brief "honeymoon period", progressively deteriorated, and the lambs died after 12 hours from severe RDS. No tracheal lesion were detected in studies lasting up to 3 days.

The ventilation method of the present invention was found to be distinct from high frequency ventilation and its variants, inasmuch as relatively normal tidal volumes are used in proportion to the remaining healthy lung mass. The method of the present invention allows pulmonary ventilation at high rates, with a markedly reduced effective anatomical dead space; it results in normal airway pressures, no evidence of lung injury, and a low mPAP.

It is believed intratracheal ventilation will impact patient management before, and during all stages of current practices in MV.

In its simplest form as described herein, intratracheal ventilation according to the present invention involves the insertion of a catheter tube into the trachea and the lungs through which a fresh air and oxygen mixture is passed. Although ideally the rate of air/oxygen flow should be selected on the basis of the medical condition of the patient and the optimum treatment protocol, it has been discovered that at high gas flow rates, which may be ideal for a particular treatment protocol, the pressure created by a stream of fresh air and oxygen may result in some back pressure, which can impair expiration and keep the lungs continuously overinflated. This impairment can be of significant concern in patients with acute respiratory failure, and chronic respiratory failure and in whom conventional means of ventilation no longer suffices.

To overcome the problem of back pressure, which causes overinflation of the lungs, and to provide a way of controlling intratracheal airway pressures during the entire respiratory cycle, the tip of the catheter was modified as described below with reference to FIGS. 3A-3B.

Figure 3A:
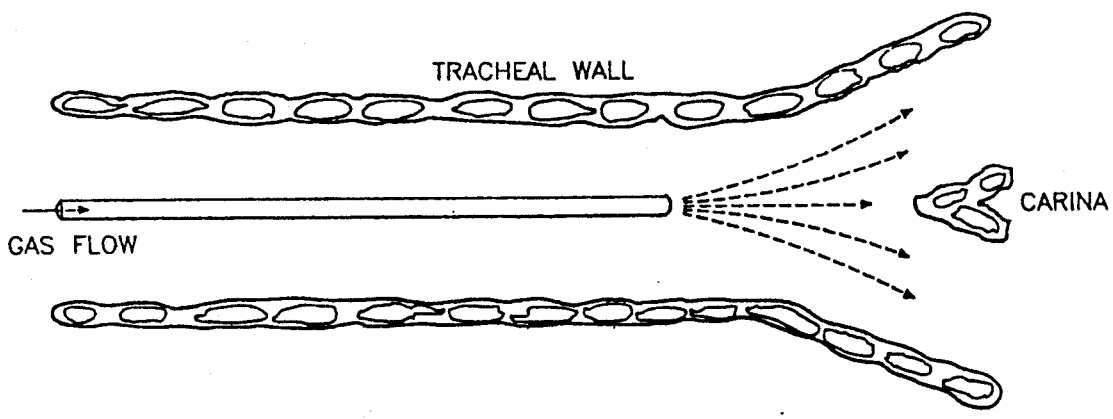
FIG. 3A is a schematic diagram illustrating an open ended catheter.

FIG. 3A is a schematic diagram illustrating an open ended catheter. In the case of positioning the open ended catheter of FIG. 3A in an area near the carina of a patient and supplying fresh air and oxygen through the catheter, high airway pressures are created which tend to keep the lungs overinflated.

Figure 3B:
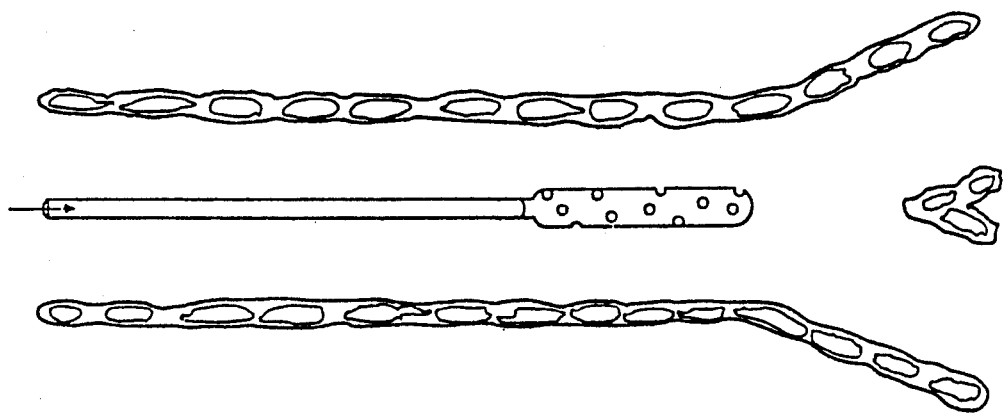
FIG. 3B is a schematic diagram illustrating a catheter having a diffuser tip.

FIG. 3B is a schematic diagram illustrating a catheter having a diffuser tip as discussed and illustrated in FIGS. 1 and 2 above. The use of a diffuser, as illustrated in FIG. 3B serves to distribute the fresh air and oxygen into the trachea while eliminating the distal jet effect provided by the open ended catheter as illustrated in FIG. 3A. By avoiding the distal jet effect, the use of the diffuser was found to significantly reduce the distal airway pressures.

Figure 3C:
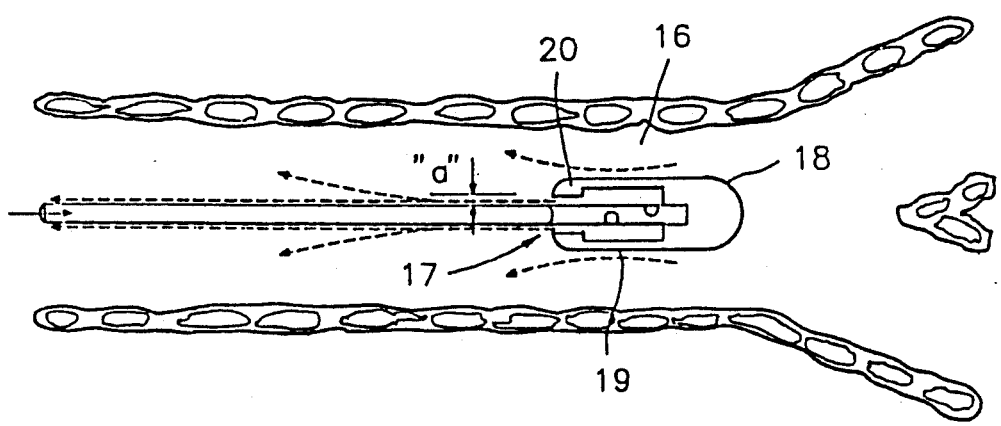
FIG. 3C is a schematic diagram illustrating a catheter having a tip according to one embodiment of the present invention.

FIG. 3C is a schematic diagram illustrating a catheter having a tip according to one embodiment of the present invention. In order to provide more versatility for intratracheal ventilation, the catheter tip 16, illustrated in FIG. 3C was developed to provide a controlled low pressure zone near the carina.

The catheter tip 16 is designed to direct the flow of air and oxygen exiting from the end of the catheter away from the carina. Accordingly, catheter tip 16 includes a gas exit port 17 which directs the flow of air and oxygen away from the distal end 18 of the catheter tip. In a preferred embodiment, the catheter tip includes a tubular portion 19 having a closed distal end 18 which is fixed to the end of catheter 1. In this preferred embodiment, the tubular portion 19 has a opened end 20 which defines an annular opening or gas exit port 17 as illustrated. The end of the catheter 1 which is enclosed by the tubular portion of the catheter tip includes a number of openings through which air and oxygen pass from the catheter 1 and through the exit port 17.

In the embodiment of the catheter tip illustrated in FIG. 3C, the gap "a" of the annular opening or exit port 17 determines the flow-pressure characteristics at the level of the carina for any given gas flow rate. Accordingly, the gap "a" may be selected to provide a particular desired pressure at the level of the carina.

Although the catheter tip 16 illustrated in FIG. 3C is depicted as having an annular opening or exit port 17, it is to be understood that both ends of the tubular portion 19 may be closed as long as there are provided one or more exit holes in end 20 which direct the flow of air and oxygen in a direction which is opposed to the distal end 18 of the catheter tip 16. That is, although preferred, it is not necessary to utilize a annular opening or exit port. The essential feature is providing a means which directs the air and oxygen in a direction opposed from the distal end 18 of the catheter tip 16.

When positioned near the carina as illustrated and utilized, the catheter tip 16 causes the full thrust of air and oxygen flowing therethrough to be directed away from the carina, hence keeping intratracheal pressure low. By keeping gap "a" in the exit port small, e.g, 0.005 to 0.020 inches, the resulting acceleration in gas flow results in a lower pressure zone, caused by Bernoulli's effect. This effect tends to entrain gases. As a result, the pressure in the distal trachea at the level of the carina can be lowered to below atmospheric pressure even at relatively low gas flows; and substantially below atmospheric pressure at higher gas flow rates.

In testing the design of the catheter tip, a mock test was preformed for each of the catheter tips illustrated in FIGS. 3A-3C. Utilizing a set flow rate of 20 l/min. through the catheter, the measured pressure level at the carina for the catheter tip illustrated in FIG. 3A was +4 cm $H_2O$. The measured pressure level at the carina for the catheter tip illustrated in FIG. 3B was +2 cm $H_2O$. The measured pressure level at the carina for the catheter tip illustrated in FIG. 3C, with a gap "a" of 0.015, was −8 cm $H_2O$.

In further tests it was determined that the catheter tip illustrated in FIG. 3C produced sub-atmospheric pressures at all gas flow rates.

While oftentimes there is a medical need to provide for some positive end expiratory pressure, the design of the catheter tip of the present invention provides the latitude to change end expiratory pressure levels which are suitable to individual needs.

Although the present invention has been described with reference to particular means, materials and embodiments, from the foregoing description, one skilled in the art can ascertain the essential characteristics of the present invention and various changes and modifications may be made to adapt the various uses and characteristics thereof without departing from the spirit and scope of the present invention as described in the claims which follow.

What is claimed is:

1. A method of providing ventilatory assistance to a patient which comprises:
   positioning a distal end of a catheter in an area near the carina of a patient;
   supplying a continuous supply of an oxygen containing gas mixture to the patient through the catheter;
   providing a tubular member attached to the distal end of said catheter;
   providing said tubular member with a closed distal end and a proximal end having at least one exit hole directed toward the proximal end of said catheter;
   attaching said tubular member to the distal end of said catheter;

leaving a gap between the exterior wall of said catheter and the interior said tubular member;

creating a sub-atmospheric pressure beyond the distal end of said catheter, near the patient's carina by directing said continuous supply of oxygen containing gas through said catheter, out the distal end of said catheter, through said gap and said at least one exit opening in a direction towards the proximal end of said catheter.

2. A method of providing ventilatory assistance accordingly to claim 1, further comprising the step of choosing a pressure at which to deliver said oxygen containing gas so as create the desired sub-atmospheric pressure near the patient's carina.

3. A method of providing ventilatory assistance according to claim 1, further comprising the step of providing said gap as an annular opening.

4. A method of providing ventilatory assistance according to claim 3, further comprising the step of providing said annular opening with a radial gap of between about 0.005 to 0.020 inches.

5. A method of providing ventilatory assistance according to claim 1, further comprising the step of creating a sub-atmospheric pressure between 0 and −8 cm $H_2O$.

6. A means for creating a sub-atmospheric pressure near the carina of a patient, said means comprising:

a catheter having a proximal end, a distal end, and an exterior wall surface;

a tubular member attached to the distal end of said catheter, said tubular member having an interior surface, a proximal end, a distal end, and at least one exit opening on the proximal end of said tubular directed toward the proximal end of said catheter;

a gap between the exterior wall surface of said catheter and the interior surface of said tubular member; and a supply of gas flowing from the proximal end of said catheter, through said catheter, out the distal end of said catheter, along the interior surface of said tubular member, out the at least one exit opening, and through said gap towards said proximal end of said catheter.

7. A catheter according to claim 6, wherein said at least one exit port comprises an annular opening.

8. A catheter according to claim 7, wherein said annular opening has a gap of between about 0.005 and 0.020 inches.

* * * * *